United States Patent
Trombetta et al.

[11] Patent Number: 5,961,757
[45] Date of Patent: Oct. 5, 1999

[54] PROCESS FOR MAKING AN ABSORBENT COMPOSITE WEB

[75] Inventors: Liberatore A. Trombetta, Silvi; Dennis A. Darby, Pescara, both of Italy

[73] Assignee: The Procter & Gamble Company, Cincinnati, Ohio

[21] Appl. No.: 09/170,506

[22] Filed: Oct. 13, 1998

Related U.S. Application Data

[62] Division of application No. 08/867,868, Jun. 2, 1997, Pat. No. 5,873,963.

[51] Int. Cl.$^6$ .............................. A61F 13/15; B32B 3/10
[52] U.S. Cl. ...................... 156/62.2; 156/73.2; 156/308.2
[58] Field of Search .................................. 156/62.2, 73.2, 156/167, 181, 252, 293, 308.2, 148

[56] References Cited

U.S. PATENT DOCUMENTS

| | | |
|---|---|---|
| 3,034,180 | 5/1962 | Greiner et al. . |
| 4,741,941 | 5/1988 | Englebert et al. . |
| 5,628,844 | 5/1997 | Nishinio et al. . |

*Primary Examiner*—Sam Chaun Yao
*Attorney, Agent, or Firm*—Theodore P. Cummings; Steven W. Miller; Jacobus C. Rasser

[57] ABSTRACT

The present invention relates to a process of making a multi-layered absorbent composite web. The web comprises at least a primary material and a secondary material. The primary material comprises apertures wherein fibers from the secondary material are inserted for fluid capture and transport. The secondary material may form a layer on the primary material once the apertures of the primary material are filled. That is, the secondary material may form a layer of material placed adjacent to the bottom surface of the primary material.

11 Claims, 5 Drawing Sheets

PROCESS FOR MAKING AN ABSORBENT COMPOSITE WEB

This application is a division of 08/867,868, filed on Jun. 2, 1997, now U.S. Pat. 5,873,963.

FIELD OF THE INVENTION

The present invention relates to a method for making an absorbent composite web having a primary material with apertures extending therethrough and a secondary material that at least fills the apertures and that may also form a layer adjacent to the bottom surface of the primary material.

BACKGROUND OF THE INVENTION

It has long been known in the disposable absorbent article art that it is extremely desirable to construct absorptive devices such as disposable diapers, catamenial pads, sanitary napkins, incontinence briefs, incontinence pads, and the like, which present a dry surface feel to the user for improving wearer comfort and to minimize the development of undesirable skin conditions due to prolonged exposure to moisture absorbed within the absorbent article. Accordingly, it is generally desirable to promote fluid transfer in a direction away from the wearer and into an absorbent element, while resisting fluid transfer in the reverse direction.

Conventional absorbent articles typically include an absorbent element (sometimes referred to as an absorbent core) interposed between a fluid pervious body-contacting element (sometimes referred to as a topsheet or an overwrap) and a fluid impervious protective barrier (sometimes referred to as a backsheet). The absorbent element is, of course, intended to receive and contain body fluids such as menses and urine. The body-contacting element is intended to provide more or less comfortable and dry-feeling contact with body surfaces while allowing free passage of fluids therethrough and into the absorbent element. The protective barrier is intended to prevent body fluids, which are expelled or which escape from the absorbent element, from soiling the user's garments.

The comfort of the user is enhanced if the absorbent article, in addition to its properties of high fluid transmisivity and fluid retention, exhibits the characteristic of unidirectional fluid transmisivity. This will improve what is known as the rewet characteristic of the absorbent product. Fluid should quickly and easily transmit through the topsheet and into the absorbent core. As the absorbent core becomes saturated, fluid will tend to pass back through the absorbent article, or rewet, causing user discomfort. As the absorbent core becomes increasingly saturated during use or is subjected to a pressure, there will be a tendency of the fluid to transmit back through the cover, or rewet the cover's surface and hence the body of the user. This discomfort caused by rewetting can cause the user to discard the absorbent product before its useful life has terminated. Therefore, it is desirable to inhibit such rewetting and thereby reduce user discomfort.

SUMMARY OF THE INVENTION

The present invention provides a process for forming an absorbent composite web. The process preferably comprises the steps of:

a) delivering a plurality of first fibers to a patterned screen having a plurality of raised portions thereon;

b) laying the first fibers onto the patterned screen to form a primary material having a top surface and a bottom surface;

c) removing the primary material from the patterned screen, the primary material having apertures corresponding to the raised portions of the patterned screen; and d) filling the apertures of the primary material with a plurality of second fibers.

Preferably, the process further provides the step of laying said plurality of second fibers onto the bottom surface of the primary material to produce a secondary material positioned adjacent to the primary material. The secondary material has an upper surface placed adjacent to the bottom surface of the primary material and a lower surface positioned away from the primary material.

The process further preferably provides the step of bonding the primary material and the secondary material by bonding or attachment means to form a bonded, multi-layered absorbent composite web. The attachment means may be selected from the group consisting of thermal bonding, ultrasonic bonding, dynamic mechanical bonding, adhesive bonding, mechanical bonding, and combinations thereof.

The raised portions of the patterned screen comprise shapes selected from the group consisting of pyramidal shapes, conical shapes, oval shapes, cylindrical shapes, spherical shapes, rectangular shapes, polygonal shapes and combinations thereof, to thereby produce like-shaped apertures within the primary and/or secondary materials.

In the process herein the first fibers of the primary material may preferably comprise nonwoven fibers selected from the group consisting of monocomponent fibers, bicomponent fibers, tricomponent fibers and combinations thereof The second fibers of the secondary material may preferably comprise a combination of synthetic fibers, synthetic material and/or cellulosic fibers. The secondary material most preferably comprises a synthetic fiber and/or material to cellulosic fiber ratio of 10 to 90. The synthetic fibers comprise at least one fiber selected from the group consisting of polyolefin, polyethylene, polypropylene, polyester and combinations thereof. The secondary material may also comprise synthetic material like polyamines, superabsorbent polymers and combinations thereof in place of or in combination with the synthetic fibers mentioned above. The cellulosic fibers used herein preferably comprise at least one fiber selected from the group consisting of comminuted wood pulp, creped cellulose wadding and combinations thereof The cellulosic fibers herein may be chemically stiffened, crimped cellulosic fibers.

In an alternative embodiment herein, the secondary material may further comprise an element selected from the group consisting of absorbent gelling material, zeolite, charcoal, silica, cyclodextrins and combinations thereof In an alternative embodiment herein, the primary material may be pre-formed. A process for forming an absorbent composite web using a pre-formed primary material comprises the following steps:

a) laying a pre-formed primary material onto a forming apparatus, the preformed primary material having a top surface, a bottom surface and a plurality of apertures extending from the top surface to the bottom surface of the primary material; and b) filling the apertures of the pre-formed primary material with a plurality of second fibers.

This alternative process may further comprise the step of laying said plurality of second fibers onto the bottom surface of the pre-formed primary material to produce a secondary material positioned adjacent to the pre-formed primary material. The secondary material has an upper surface that is placed adjacent to the bottom surface of the pre-formed primary material and a lower surface positioned away from the pre-formed primary material.

Preferably the pre-formed primary material and the secondary material are bonded together by bonding or attachment means to form a bonded, multi-layered absorbent composite. Suitable bonding means may include thermal bonding, ultrasonic bonding, dynamic mechanical bonding, adhesive bonding, mechanical bonding, and combinations thereof.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE DRAWINGS

As used herein, the term "absorbent article" refers to devices which absorb and contain body exudates, and, more specifically, refers to devices which are placed against or in close proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

The Process

The present invention provides a process for forming an absorbent composite web. The process comprises the steps of:

a) delivering a plurality of first fibers to a patterned screen having a plurality of raised portions thereon;

b) laying the first fibers onto the patterned screen to form a primary material having a top surface and a bottom surface;

c) removing the primary material from the patterned screen, the primary material having apertures corresponding to the raised portions of the patterned screen; and d) filling the apertures of the primary material with a plurality of second fibers.

Figure 1:
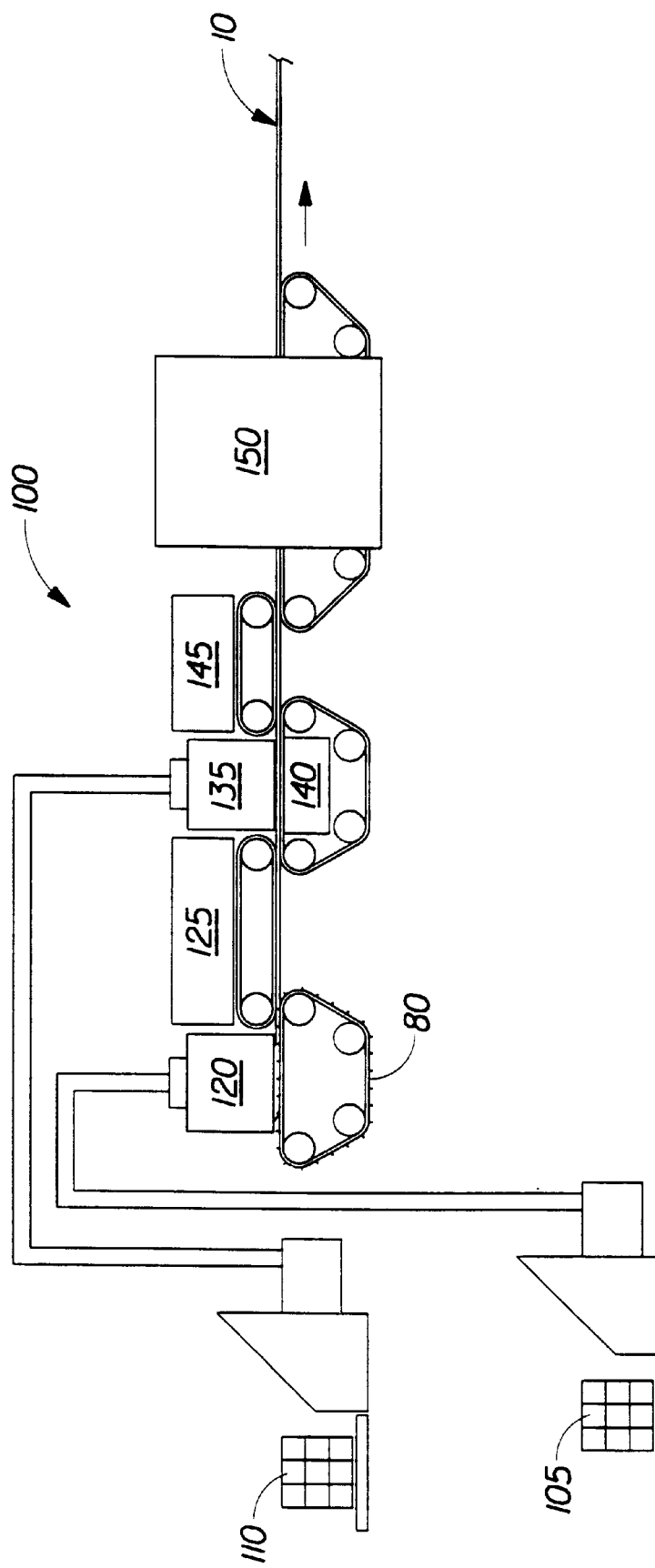
FIG. 1 is a simplified view of a preferred process of the present invention.

FIG. 1 shows a preferred process 100 whereby a first fiber bail 105 comprised of a substantially moisture-insensitive fiber, preferably being a bi-component fiber, is loaded into a feeding element for transfer of the fibers to the first forming head 120. The first forming head 120 is responsible for laying (i.e., airlaying) the fibers onto the patterned screen 80 that comprises one or more types of raised portions 70 (see FIGS. 3, 4A, 4B & 4C). In practice, the fibers from the first fiber bail 105 are metered out onto the patterned screen 80 between the raised portions 70 to create a primary material 15 that is fibrous and has apertures extending therethrough (FIG. 2); i.e., apertures are created within the primary material 15 from the raised portions 70 on the patterned screen 80. A suitable process for airlaying the fibers herein into the web 10 at both forming heads 120 and 135 is disclosed in PCT Application WO 96/07792 published on Mar. 14, 1996 to Mosgaard, such disclosure being incorporated herein by reference.

Once the apertures 25 are formed within the primary material 15, the material 15 is suctioned away from the patterned screen 80 by a first vacuum 125. The first vacuum 125 lifts the primary material 15 from the patterned screen 80 and transports the primary material 15 to the second forming head 135.

At the second forming head 135, a combination synthetic fiber and cellulosic fiber blend is laid onto the bottom surface 18 (see FIG. 2) of the primary material 15. Any one of the synthetic materials mentioned above may also be used in the process shown in FIG. 2, e.g., an absorbent material such as a functional absorbent material may be used. Preferably, a second vacuum 140 lays beneath the second forming head 135 and the primary material 15. This second vacuum 140 draws the fibers from the second fiber bail 110 into the apertures 25 of the primary material 15. Once the apertures 25 are filled, the cellulosic/synthetic fiber blend may preferably continue to be laid onto the bottom surface 18 of the primary material 15, thereby forming a secondary material layer that is fibrous (see FIG. 2).

The primary and secondary materials herein may not be bonded to one-another at their forming by a bonding or attachment means. Preferably, however, the materials 15 and 20, respectively, may be bonded by a bonding means such as any of the known compatible adhesives known in the art or through heating the composite web together. For bonding the primary and secondary materials together through heat, thermobondable fibers may be used between and/or through the primary and secondary materials to help form thermal bonds between them at their heating. PCT Application No. WO 95/18886 published on Jul. 13, 1995 to Mosgaard, et al. discloses the heating of a web with thermobondable fibers therein to aid in its bonding, such disclosure being incorporated herein by reference.

FIG. 1 further discloses a means for transporting a pre-bonded absorbent composite web 10 to a bonding means 150. By the term "pre-bonded" it is meant herein the state of a web prior to its bonding by an outside bonding means; it is not meant to suggest that the web may not possess some measure of bonding betwixt the primary and secondary materials themselves. In the preferred process herein, a third vacuum 145 transports the web 10 to a bonding means 150. As has been previously mentioned, a bonding means 150 may comprise any of those conventional means known in the art; e.g., thermal bonding, ultrasonic bonding, adhesive bonding, a combination of these, etc. Once the web 10 moves through the bonding operation, the formed absorbent composite web 10 is in an externally bonded state; i.e., bonded together by outside means.

In a preferred embodiment herein, a vacuum like the vacuum 140 shown in FIG. 1 may be placed beneath the first forming head 120. This vacuum would preferably be used to draw the primary material, preferably being fibers from the first forming head 120 onto the patterned surface 80. Furthermore, the vacuum under the first forming head 120 would hold those fibers onto the patterned surface 80. Also preferably, there may be multiple forming heads for the distribution of various types of fibers varying in composition, denier, caliper, length, diameter, texture and any other type of varying fiber characteristic. These multiple forming heads may rotate into and out of position along the process path as specified, or they may be formed in series along the process path. It is noted, however, that neither the alignment or configuration of the forming heads forms any part of the enclosed invention and may be manipulated and configured in any number of ways to suit the design intent of one skilled in the art.

In an alternative embodiment herein, the primary material may be pre-formed. A process for forming an absorbent composite web using a pre-formed primary material comprises the following steps:

a) laying a pre-formed primary material onto a forming apparatus; the pre-formed primary material has a top surface, a bottom surface and a plurality of apertures extending from the top surface to the bottom surface of the primary material; and
 b) filling the apertures of the pre-formed primary material with a secondary material preferably being fibers.

This alternative process may further comprise the step of laying a plurality of secondary material preferably comprising fibers 22 onto the bottom surface 18 of the pre-formed primary material 15 to produce a secondary material 20 positioned adjacent to the pre-formed primary material 15. The secondary material 20 has an upper surface 21 that is placed adjacent to the bottom surface 18 of the pre-formed primary material 15 and a lower surface 23 positioned away from the pre-formed primary material 15.

Preferably the pre-formed primary material 15 and the secondary material 20 are bonded together by attachment means to form a bonded, multi-layered absorbent composite. Suitable attachment means may include thermal bonding, ultrasonic bonding, dynamic mechanical bonding, adhesive, mechanical bonding, and combinations thereof.

In another alternative embodiment herein, first fibers 17 may be laid down onto a screen that is flat and therefore devoid of any raised portions. Once these fibers have been laid down, they form the primary material 15 and are delivered to a means which will perforate the material 15, thus providing apertures within the primary material 15 without using a patterned screen. After forming the apertures by the perforating means, the primary material 15 is delivered to a means that will lay the second fibers 22 onto it to thereby produce a secondary material 20. This process would also work equally well for a pre-formed primary material; i.e., the pre-formed material would be laid down, perforated by a perforating means and then delivered to means whereby a secondary material like absorbent fibers, would be laid onto the pre-formed, perforated primary material. This perforation process is disclosed in U. S. Pat. No. 4,780,352 issued on Oct. 25, 1988 to Palumbo and is incorporated herein by reference.

The Absorbent Composite Web

Figure 2:
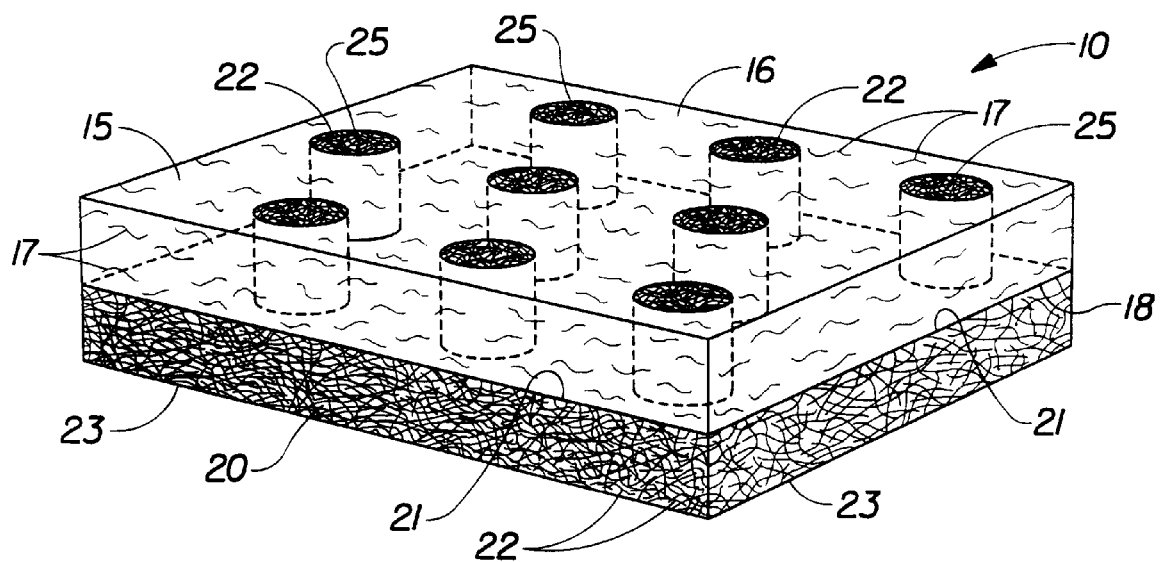
FIG. 2 is a perspective view of the absorbent composite web of the present invention.

FIG. 2 provides a perspective view of the web 10 or absorbent composite web 10. By the terms "web" and "absorbent composite web" it is meant herein a multi-layered absorbent or fluid transporting and retaining structure made of two or more distinct parts where at least one part of the structure functions primarily to transport fluid. The web 10 preferably comprises a primary material 15 formed by a plurality of first fibers 17. The primary material 15 further comprises a top surface 16 which preferably faces toward a user when the web 10 is worn in the undergarment of a user. Opposite of the top surface 16 is the bottom surface 18 of the primary material 15. As is seen in FIG. 2, the primary material 15 is formed in such a way as to provide apertures 25 throughout the primary material 15. These apertures 25 extend from the top surface 16 to the bottom surface 18 of the primary material 15. The apertures 25 may be randomly assigned throughout the primary material 15 or they may be located in any organized or regular configuration conceivable throughout the primary material 15. Preferably, the apertures 25 will be regularly shaped from top to bottom. Also, the apertures 25 may comprise a wider opening at the top surface 16 than at the bottom surface 18 and the reverse also is true.

The secondary material 20 is formed from a plurality of second fibers 22. The secondary material comprises an upper surface 21 and a lower surface 23. The upper surface 21 of the secondary material 20 is held adjacent to the bottom surface 18 of primary material 15. As is clearly seen in FIG. 2, the secondary material 20 not only forms a layer that is adjacent to the bottom surface 18 of the primary material 15, but also is inserted within the apertures 25 of the primary material 15. Therefore, as fluid insults or contacts the top surface 16 of the primary material 15, it will also immediately insult at least a portion of the secondary material 20, i.e., those portions within the apertures 25.

FIG. 2 provides a view in which the secondary material 20 located within the apertures 25 appears to be at equal level to the top surface 16 of the primary material 15. This is a preferred embodiment, however, the secondary material 20 may extend from about one-fourth from the base of an aperture 25 to about the total height of an aperture 25. However, for premium performance, it is believed herein that the level of the secondary material 20 within an aperture 25 should be approximately equal to the top surface 16 of the primary material 15.

Preferably, the first fibers 17 used to form the primary material 15 are moisture insensitive. By the term "moisture insensitive" it is meant herein that the fibers will substantially not absorb any fluid within its structure and further will not collapse as a result of fluid insult. Furthermore, the first fibers 17 will remain intact upon liquid insult and most importantly will not retain any liquid. The objective of the first fibers 17 is to collect fluid quickly and transport it just as quickly out of its structure to the second fibers 22 of the secondary material 20 for storage. To further accommodate this transport function of the primary material 15, the density of the primary material 15 is preferably less than the density of the secondary material 20.

While the density of the primary material 15 is preferably less than the density of the secondary material 20, it should be noted that the void volume, which is the inverse of density herein, if preferably higher for the primary material 15 than for the secondary material 20. In practice, void volume relates to the amount of voids or spaced volume (i.e., spaces) per gram of fibers. It is desirable that there be more open spaces in the primary material 15 than the secondary material 20 to create a density gradient across the two materials whereby fluid is readily and quickly suctioned from the primary material to the secondary material. As has been noted above, the primary material 15 is to be fashioned in such a way as to enable its structure to quickly receive fluids and then transport them to the secondary material 20 without the collapse of the primary material 15. In this fashion, the primary material 15 will then be able to receive multiple fluid insults and then transfer such fluids to the secondary material 20.

Generally, because the material within apertures 25 and the secondary material layer positioned below the primary layer comprise the same fibers, i.e., the second set of fibers 22, each will have approximately the same density. However, either the secondary material within apertures 25 or the secondary material layer positioned below the primary layer may be further densified through compaction or the addition of certain elements which may include, but are not limited to, absorbent gelling material, superabsorbent polymers, silica, perfume, cyclodextrins, thermobondable fibers, charcoal, zeolite etc. For example, in one embodiment, the secondary material may be densified by elements which then cause it to have a greater density than both the primary material 15 and the material within apertures 25. In such an embodiment, density gradients are established across the primary material 15 to the secondary material 20 as well as across the material within apertures 25 to the secondary material 20 positioned below the primary layer; this is a preferred embodiment. Also, the material within apertures 25 may be made to be more dense than the secondary material 20.

In an alternative embodiment herein, the densities for each component of the web 10 may have densities which are all approximately equal. In such a case, there is little or no discernible density gradient established across the primary material 15, the secondary material layer or the material within apertures 25.

Preferably, the secondary material 20 will have a greater basis weight than the primary material 15. This corresponds to the secondary material 20 also preferably having the greater density than the primary material 15 and helps to ensure that a density gradient from the primary material 15 to the secondary material 20 is established.

The calipers for both the primary material 15 and the secondary material 20 are in the ranges of 0.5 to 10 mm, preferably 1 to 5 mm and more preferably 1.5 to 2.0 mm. The basis weights for the primary material 15 and the secondary material 20 are in the ranges of 20–3000 g/m$^2$, preferably 40–1000 g/m$^2$ and more preferably 50–300 g/m$^2$.

In an alternative embodiment herein, density gradients are created within either the primary material 15, the secondary material 20 or both. When a density gradient is established within the primary material 15, it relates also to the varying pore sizes established throughout the primary material 15 and is thus also referred to as the pore size gradient. The density within the primary material 15 may be made to be less dense towards its top surface 16 and more dense towards the upper surface 21 of the secondary material 20, i.e., the bottom surface of the primary material 15. This inner densification may be performed by compacting the fibers within the primary material 15 and/or through forming the primary material 15 from like or similar fibers of varying denier, i.e., the coarseness or fineness of a fiber.

In like fashion, the secondary material 20 may be inner densified whereby the portion of the material 20 closest to the upper surface 21 is less dense than the portion nearest to the lower surface 23 of the secondary material 20. Again, this inner densification may be performed through compaction of the fibers within the secondary material 20 and/or through forming the secondary material 20 from like or similar fibers of varying denier, i.e., the coarseness or fineness of a fiber.

The varying denier of the fibers within a material establishes the density or pore size gradient within the materials. Preferably, higher denier fibers and/or a mixture comprising a higher percentage of coarser fibers, will reside closest to the top and upper surfaces of the primary and secondary materials. Lower denier fibers will then therefore preferably reside closest to the lower or bottom surfaces of the primary and secondary materials. Such preferred construction creates primary and secondary materials that are less dense at their upper surfaces and more dense at their lower surfaces. Specifically, the coarser upper fibers (i.e., those having higher deniers) are more resilient and less structurally compressive and thus allow for the creation of greater void volumes in the upper surfaces of a material. Finer upper fibers (i.e., those having lower deniers) are less resilient and more structurally compressive and thus allow for the creation of greater compaction and fewer void volumes in the lower surfaces of a material. It is preferred herein that the lower or bottom portions of a material be more dense and that their upper portions be less dense to receive fluids quickly, thereby pulling them away from the top surfaces and holding them within the lower surfaces of a material away from its upper surfaces.

Figure 7:
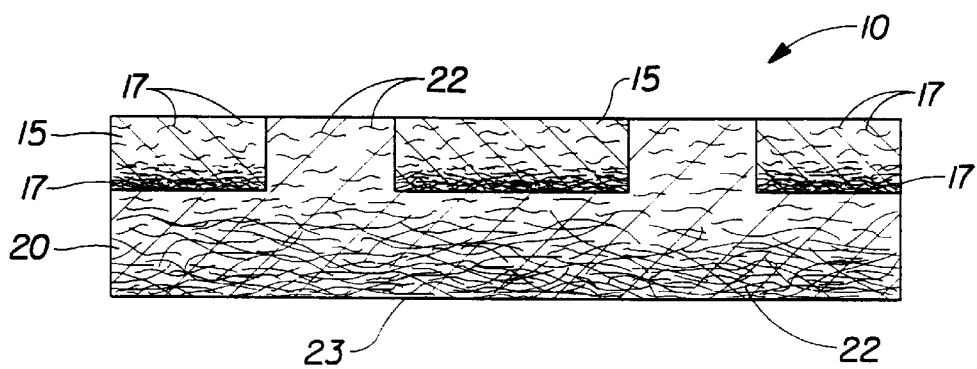
FIG. 7 is a cross-sectional view of an alternative embodiment of a composite web.

FIG. 7 shows a cross-sectional view of a web 10 having primary material 15 and a secondary material 20 that have been inner densified with fibers 17 and fibers 22, respectively. As has been mentioned above, this inner densification may have occurred either through compaction of the fibers and/or through the inclusion of fibers of varying deniers. It should be noted herein that though the primary material 15, for example, may comprise fibers 17 of varying deniers, the basis weights of the fibers are all approximately equal. That is, the basis weights of the fibers do not vary as the denier of the fibers within a material varies. It is further noted that the inner densification of fibers may occur by the use of varying fiber types having different weights, thicknesses, bulk densities and other attributes that may affect density within the materials 15 and 20.

The primary material 15 may also be formed from a nonwoven web which may be a spunbonded web, a meltblown web, a bonded carded web, or a thermally bonded airlaid web. The nonwoven web may be made of fiber forming polymers such as, for example, polyesters, polyamines, and polyolefins. Exemplary polyolefins include one or more of polypropylene, polyethylene, ethylene copolymers, propylene copolymers, and butene copolymers.

In another preferred embodiment, the nonwoven web may comprise bicomponent fibers. The bicomponent fiber used herein is preferably a thermobondable bicomponent fiber having an inner core component and outer sheath component where the inner core component has a higher melting point than the outer sheath component. The fiber is typically hydrophobic, but can be made hydrophilic by incorporating a surfactant into the sheath of the bicomponent fiber and/or by treating the external surface of the sheath with a surfactant. Exemplary bicomponent fibers and processes for producing the same are described in U.S. Pat. No. 5,456,982 entitled "Bicomponent Synthesis Fibre And Process For Producing Same", issued to Hansen et al. on Oct. 10, 1995 and U.S. Pat. No. 5,603,707 entitled "Absorbent Article Having A Rewet Barrier", issued to Trombetta et al. on Feb. 18, 1997, each of which patents are incorporated herein by reference. Whatever bicomponent fiber is used herein, it must be substantially moisture insensitive so as not to absorb an amount of fluid that would either hinder rewet of the primary material 15 or cause the structural integrity of the primary material 15 to collapse or be otherwise compromised.

The primary material 15 should have an operable level of density and basis weight to rapidly acquire and then drain liquid surges into the underlying secondary material 20, thus remaining substantially empty to receive subsequent liquid surges, i.e., insults. The primary material 15 should have sufficient void volume capacity to temporarily retain the amount of liquid that is typically discharged by a wearer during a single insult or surge of liquid into the web 10. Insufficient void volume capacity may result in excessive pooling of liquid against the wearer's skin or excessive run-off of liquid. It should be noted herein that the primary material 15 preferably comprises substantially no cellulosic material or any type of absorbent fiber that would retain and not substantially transfer all of the fluid received by the primary material 15 to the secondary material 20 and/or the fibers 22 within an aperture 25.

The secondary material 20 preferably comprises from about 10 wt. % to about 90 wt. % of cellulosic material and from about 10 wt. % to about 90 wt. % of synthetic material. More preferably, the secondary material 20 comprises from about 10 wt. % of a synthetic fiber like polyolefin to about 90 wt. % of a cellulosic fiber like wood pulp. The purpose for the secondary material 20 is to create an absorbent, fluid-retaining structure for the fluid transported to the secondary material 20 by the primary material 15. This is especially true where the web 10 is the only or primary fluid absorbing and retaining structure in an absorbent article.

Suitable absorbent materials for use in the secondary material 20 are comminuted wood pulp which is generally referred to as airfelt, creped cellulose wadding; meltblown polymers including coform; chemically stiffened, modified or cross-linked cellulosic fibers; synthetic fibers such as crimped polyester fibers, polyester, polyamines and polyolefin; peat moss, tissue including tissue wraps and tissue laminates; superabsorbent polymers; absorbent gelling materials; or any equivalent material or combinations of materials, or mixtures of these.

Figure 3:
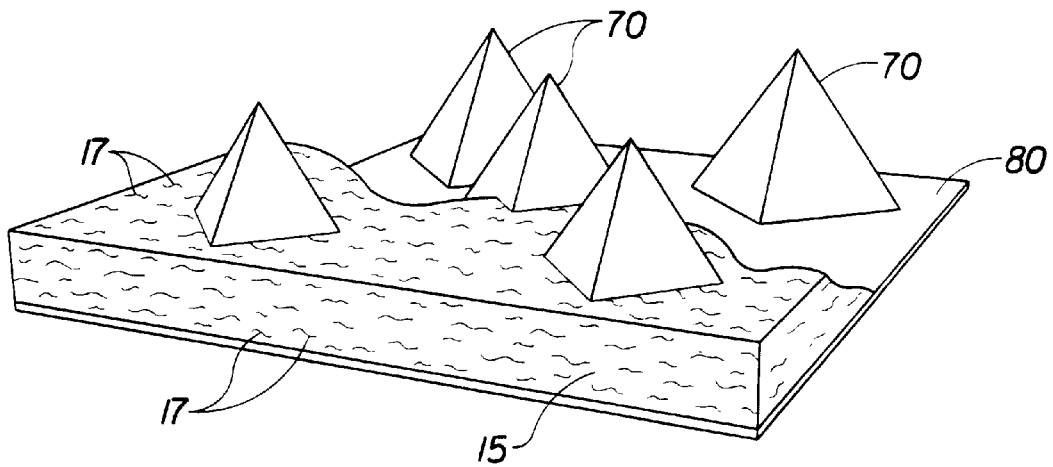
FIG. 3 is a perspective view of a portion of a patterned screen used in a process for the forming of a primary material of the present invention.
Figure 4A:
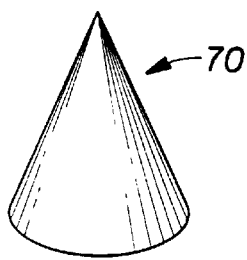
FIG. 4A is a perspective view of an alternative embodiment of a raised portion.
Figure 4B:
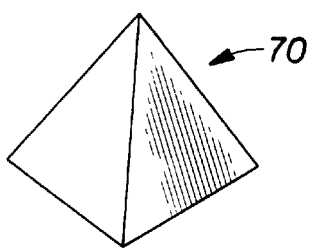
FIG. 4B is a perspective view of an alternative embodiment of a raised portion.
Figure 4C:
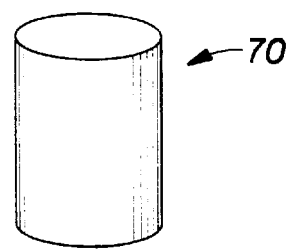
FIG. 4C is a perspective view of an alternative embodiment of a raised portion.

FIG. 3 provides a perspective view of a section of the forming process for the web 10. Specifically, a first set of fibers 17 for the primary material 15 are shown being laid down onto a patterned screen 80 having alternating raised portions 70 throughout. FIG. 3 shows the patterned screen 80 being partially filled with fibers 17, but in practice, such a screen 80 would be completely filled across with the fibers 17. Furthermore, the raised portions 70 are shown to be pyramidal in shape. However, as is shown in FIGS. 4A, 4B and 4C, the raised portions may be in any shape desired by a manufacturer, e.g., pyramidal, conical, cylindrical, polygonal, spherical, etc., to produce a desired shaped aperture 25. Aperture shapes may therefore include conical, pyramidal, polygonal, cylindrical, spherical, and any unconventional or irregular shape desired by a manufacturer. It is noted herein that several types of raised portions 70 may be used on one patterned screen 80. The type of raised portion 70 used will depend on the desired shape, contour and structure of apertures within the primary material 15.

Preferably, the top of a raised portion 70 will have a surface area that is less than or equal to the surface area of the base of that raised portion 70. More preferably the side surfaces of the raised portion 70 will provide a shear or taper away from the top of the raised portion 70. Where a raised portion 70 provides a taper away from its top (see FIGS. 4A and 4B), fibers laid down by a forming head to the patterned screen 80 will move down the sides of the tapered raised portions 70 and collect in the depressed areas on the screen 80 away from the raised portions 70. By the term "depressed areas" as used herein it is meant those areas on the screen 80 that are occupied by a raised portion 70. This mechanism is especially important when a manufacturer seeks to density a web 10 as discussed in regards to FIG. 7.

Figure 8:
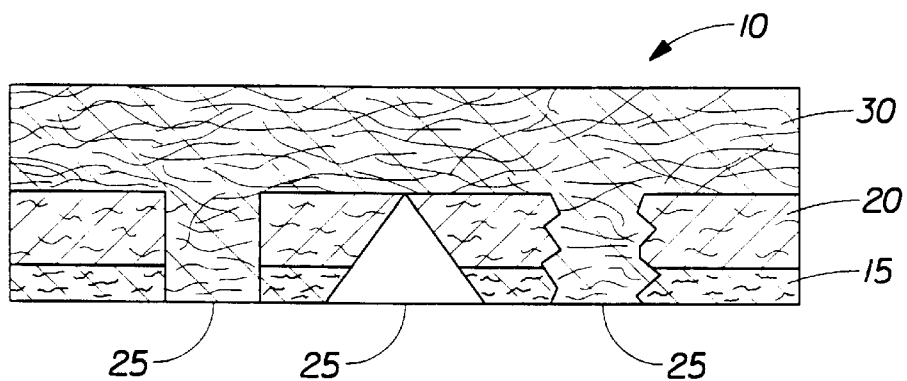
FIG. 8 is a cross-sectional view of an alternative embodiment of a composite web.

It is further noted that the height reached by the first fibers 17 laid onto the patterned screen 80 is limited. That is, the height of the fibers 17 will preferably not extend from the base to the top of any raised portion 70. Rather, the fibers 17 will be laid on the screen 80 such that there would be no substantial resistance to the second set of fibers 22 fully penetrating the apertures 25. The height of the first set of fibers 17 which form the primary material 15 is limited to ensure that the aperture opening at the lower surface 18 of the primary material 15 is sufficiently large enough to allow the substantially unresisted transfer of fibers 22 through it. The embodiment discussed in FIG. 8 is a specific type of embodiment illustrating alternatives herein and should be regarded as an exception to the above stated criteria for laying a first set of fibers 17 onto a patterned screen 80.

Figure 5:
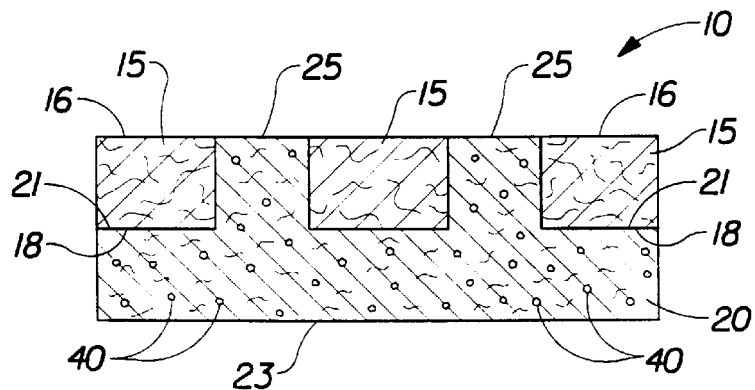
FIG. 5 is a cross-sectional view of an absorbent composite web.
Figure 5A:
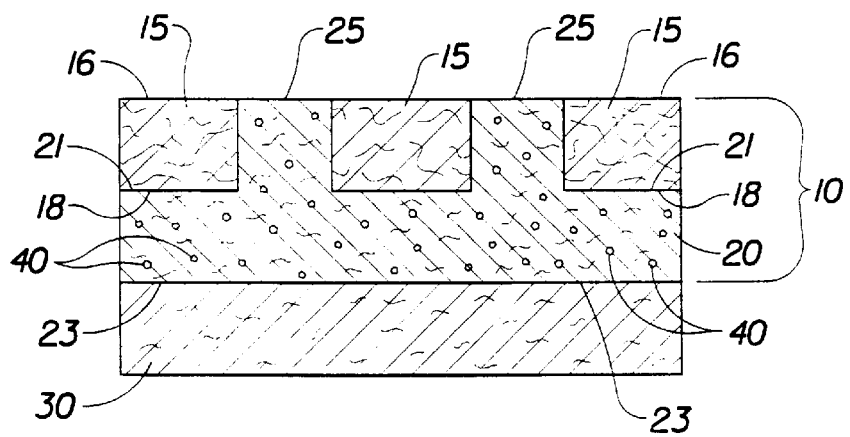
FIG. 5A is a cross-sectional view of an alternative embodiment of an absorbent composite web.
Figure 6:
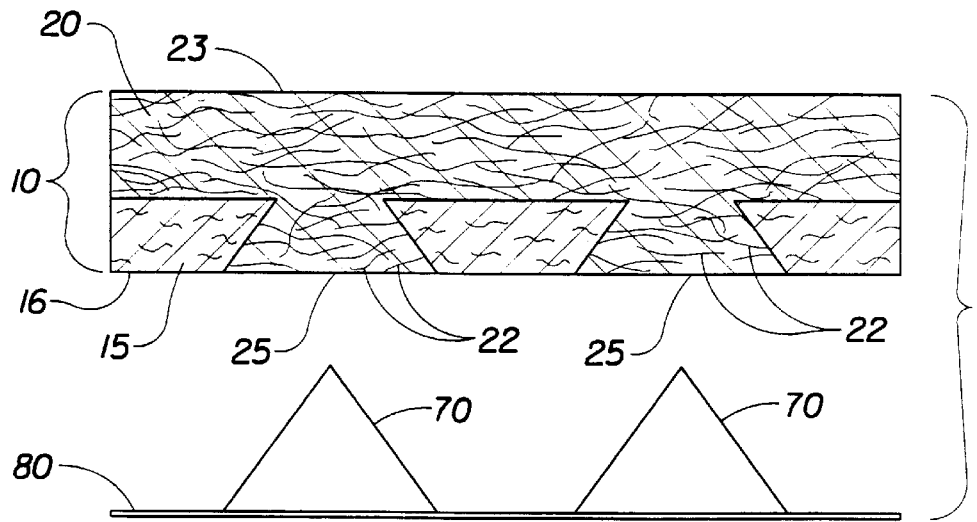
FIG. 6 is an exploded, cross-sectional view of a web forming process of the present invention.

FIGS. 5 and 5A show cross-sections of two webs 10. Both figures show the primary material 15 and the secondary material 20. FIG. 5A shows an additional absorbent material 30 positioned adjacent to the bottom surface of the secondary material 20. FIG. 5A represents an alternative embodiment herein wherein additional absorbent material is placed adjacent to the web 10. The absorbent material 30 may be the same as or similar to the absorbent material used in the secondary material 20. In an absorbent article embodiment, absorbent material 30 may represent an absorbent core of a conventional disposable absorbent article, e.g., a diaper or catamenial.

Also disclosed in FIGS. 5 and 5A are additives or elements included within the secondary material 20. The elements 40 may be materials responsible for added fluid absorption, odor control, fragrance release, bonding etc. These elements may be selected from a group consisting of absorbent gelling material, zeolite, charcoal, silica, cyclodextrins, perfume, thermobondable fibers and combinations thereof.

It is further noted herein that the web 10 may comprise as many levels or layers of material as is desired by a manufacturer. In fact, multiple layers, i.e., at least two, of differing types of fibers with varying deniers, basis weights, and material calipers may be employed as part of the invention herein.

FIG. 8 discloses an alternative embodiment herein where a web 10 comprises multiple layers or levels of materials. A primary material 15 sits adjacent to a secondary material 20 which sits adjacent to a tertiary material 30. Also, apertures 25 of varying shapes are fitted within the primary and secondary materials and lead to the tertiary material 30. These apertures 25 may either be filled with an absorbent material from fibers similar to those in the materials underlying the primary material 15, and/or the apertures 25 may be unfilled and thus serve as an immediate conduit to materials underlying the primary material 15. For example, the central aperture of the web 10, i.e., that aperture 25 having the pyramidal or conical shape, is substantially not filled with any fibers, absorbent or otherwise. This would serve to allow fluid to enter directly into the secondary material 20 and the tertiary material 30 as fluid impacts an unfilled aperture 25. It is to be noted herein that the fibers within the apertures 25 of FIG. 8 are shown as fibers from the tertiary material 30, however, these fibers may also be from the secondary material 20. It is further noted herein that any of the elements mentioned above (e.g., perfume, odor absorbers, etc.) may also be positioned within the secondary material 20 and/or the tertiary material 30 of the web 10 of FIG. 8.

A combination of unfilled and filled apertures 25 may be used in bi-layer and multi-layered absorbent composite webs 10 herein. By the term "multi-layered" it is meant a composite web herein having at least two material levels within its structure.

Suitable odor controlling and/or perfume agents are disclosed in U.S. Pat. No. 5,591,146 issued to Hasse on Jan. 7, 1997 and U.S. patent application No. 08/635,221 filed on Apr. 17, 1996, entitled "Absorbent Article With Odor Masking Agents Released By The Fastening System" and U.S. patent application No. 08/764,817 filed on Dec. 12, 1996, entitled "A Diaper Having Perfume Zones", each of which is incorporated herein by reference.

Figure 9:
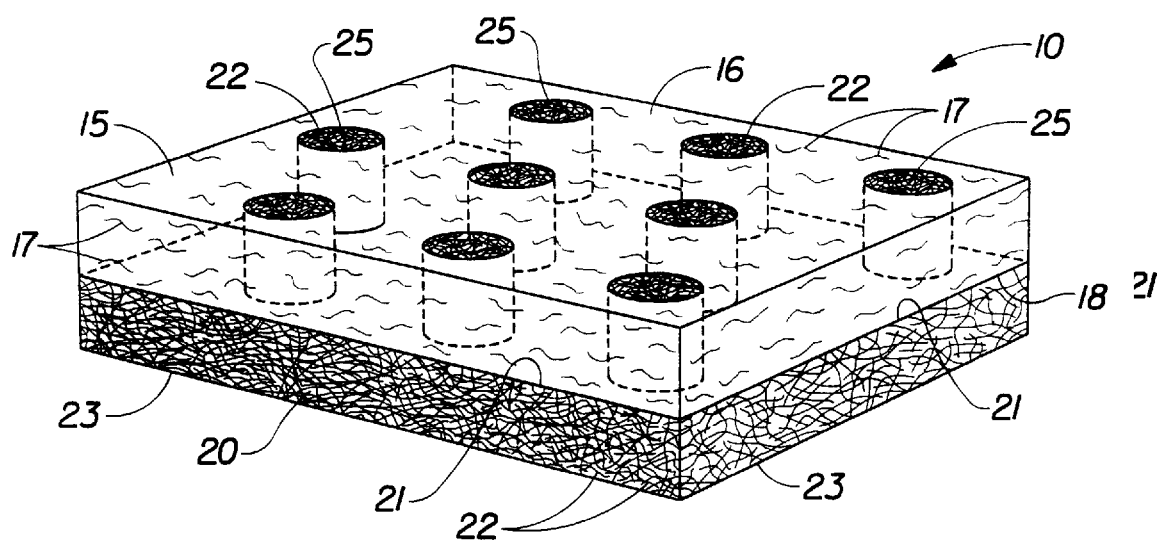
FIG. 9 is a perspective view of an alternative embodiment of the invention of a composite web.

FIG. 9 discloses an alternative embodiment wherein the apertures 25 extend from the upper surface 21 to the lower surface 23 of the secondary material 20. This is a reversal of the structure of web 10 in FIG. 2. Additionally, the fibers 17 within the apertures 25 are those fibers that make up the primary material 15. The web 10 of FIG. 9 is shown upside down whereby the lower surface 23 of the secondary material is shown facing upwards. This view of the web 10 is meant to clearly indicate the apertures 25 and the fibers 17 that are located therein. In practice, the primary material of FIG. 9 is that material facing towards a user and the secondary material faces away from a user.

While not wishing to be bound by any particular theory, it is believed herein that as fluid is acquired at the top surface 16 of the primary material 15 in FIG. 9, the fluid will travel through the apertures 25 along the fibers 17 and either into an underlying absorbent element or into the secondary material 20 for storage. It is noted herein that the web 10 of FIG. 9 is not a stand alone structure like the web 10 in FIG. 2. That is, there must be an accompanying absorbent element placed adjacent to or nearly adjacent to the lower surface 23 of the secondary material 20. It is not the intention of any embodiment herein to allow the flow of fluid through an absorbent composite web 10 herein without its capture and storage.

The process of making the embodiment disclosed in FIG. 9 is the same as that process disclosed for FIG. 2 except that the fibers 22 for the secondary material 20 are introduced by the first forming head 120. Also, the fibers 17 for the primary material 15 are introduced by the second forming head 135. That is the secondary material 20 with apertures 25 therein is formed first, and the primary material 15 is formed last. This represents a reversal in the order of production for primary and secondary materials in FIG. 2.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for forming a fluid handling absorbent composite web for use in the absorbent core of an absorbent article, said process comprising the steps of:

a) laying a pre-formed primary material onto a forming apparatus, said pre-formed primary material having a substantially flattened top surface, a substantially flattened bottom surface and a plurality of apertures extending from said substantially flattened top surface to said substantially flattened bottom surface of said primary material, said apertures having a pair of mutually opposed openings, each said opening being substantially planar with the top surface of the pre-formed primary material and the bottom surface of the pre-formed primary material; and b) filling said apertures of said pre-formed primary material with a plurality of second fibers, such that said apertures are substantially, completely filled with said second fibers.

2. The process of claim 1 further comprising the step of laying said plurality of second set of fibers onto said bottom surface of said pre-formed primary material to produce a secondary material positioned adjacent to said pre-formed primary material, said secondary material having an upper surface being placed adjacent to said bottom surface of said pre-formed primary material and a lower surface positioned away from said pre-formed primary material.

3. The process of claim 2 further comprising the step of bonding said pre-formed primary material and said secondary material by attachment means to form a bonded, multi-layered absorbent composite.

4. The process of claim 3 wherein said attachment means is selected from the group consisting of thermal bonding, ultrasonic bonding, dynamic mechanical bonding, adhesive, mechanical bonding, and combinations thereof.

5. The process of claim 1 wherein said pre-formed primary material comprises nonwoven fibers selected from the group consisting of monocomponent fibers, bicomponent fibers, tricomponent fibers and combinations thereof.

6. The process of claim 2 wherein said secondary material comprises synthetic material and cellulosic fibers.

7. The process of claim 6 wherein said secondary material comprises a synthetic material to cellulosic fiber ratio of 10 to 90.

8. The process of claim 6 wherein said synthetic material comprises at least one material selected from the group consisting of polyolefin, polyethylene, polypropylene, polyester, polyamines, superabsorbent polymers and combinations thereof.

9. The process of claim 6 wherein said cellulosic fibers comprise at least one fiber selected from the group consisting of comminuted wood pulp, creped cellulose wadding, meltblown polymers and combinations thereof.

10. The process of claim 9 wherein said cellulosic fibers are chemically stiffened, crimped cellulosic fibers.

11. The process of claim 1 wherein said secondary material may further comprise an element selected from the group consisting of absorbent gelling material, zeolite, charcoal, silica, cyclodextrins, perfume and combinations thereof.

* * * * *